United States Patent [19]

Butcher et al.

[11] Patent Number: 5,316,913
[45] Date of Patent: May 31, 1994

[54] NEUTROPHIL LECAM-1 AS INDICATOR OF NEUTROPHIL ACTIVATION

[75] Inventors: Eugene C. Butcher, Portola Valley, Calif.; Louis J. Picker, Dallas, Tex.

[73] Assignee: Stanford University, Stanford, Calif.

[21] Appl. No.: 755,749

[22] Filed: Sep. 6, 1991

[51] Int. Cl.$^5$ .......................................... G01N 33/543
[52] U.S. Cl. .................................. 435/7.24; 435/7.94; 435/975; 436/518; 436/536; 436/548
[58] Field of Search .................. 435/7.24, 7.94, 975; 436/518, 536, 548

[56] References Cited

U.S. PATENT DOCUMENTS 5,006,459 4/1991 Kung et al. ............................. 435/5

OTHER PUBLICATIONS

"Carbohydrate ligands of the LEC cell adhesion molecules" by Brandley et al. in *Cell* (1990) 63:861–863.
"Chemotactic factors regulate lectin adhesion molecule 1 (LECAM-1)-dependent neutrophil adhesion to cytokine-stimulated endothlial cells in vitro" by Smith et al. in *J. Clin. Invest.* (1991) 87:609–618.
"Identification of a human peripheral lymph node homing receptor: A rapidly down–regulated adhesion molecule" by Kishimoto et al. in *Proc. Natl. Acad. Sci. USA* (1990) 87:224–2248.
"Function and regulation of the neutrophil MEL-14 antigen in vivo: Comparison with LFA-1 and MAC-1." by Jutila et al. in *J. Immunol.* (1989) 143:3318–3324.
"Cloning of GMP-140, a granule membrane protein of platelets and endothelium: Sequence similarity to proteins involved in cell adhesion and inflammation" by Johnston et al. in *Cell* (1989) 56:1033–1044.
"The peripheral lymph node homing receptor, LECAM-1 is involved in CD18-independent adhesion of human neutrophils to endothelium" by Hallman et al. in *Biochem. Biophys. Res. Comm.* (1991) 174:236–243.
"A unique phenotype of skin-associated lymphocytes in humans" by Picker et al. in *J. Path.* (1990) 136:1053–1068.
"Quantitative investigations of the adhesiveness of the circulating polymorphonuclear leukocytes to blood vessel walls" by Atherton and Born in *J. Physiol.* (1972) 222:447–474.
"Leukocyte–endothelial cell recognition: Evidence of a common molecular mechanism shared by neutrophils, lymphocytes, and other leukocytes" by Lewinson et al. in *J. Immunol.* (1987) 138:4313–4321.
"CD11/CD18-independent neutrophil adherence to inducible endothelial-leucocyte adhesion molecules (E-LAM) in vitro" by Dobrina et al. in *Immunology* (1989) 67:502–508.
"ELAM-1 is an adhesion molecule for skin-homing T cells" by Picker et al. in *Nature* (1991) 349:796–799.
"The neutrophil selectin LECAM-1 presents carbohydrate ligands to the vascular selectins ELAM-1 and GMP-140" by Picker et al. in *Cell* (1991) 66:921–933.
"Two-step model of leukocyte–endothelial cell interaction in inflammation:Distinct roles for LECAM-1 and the Leukocyte Beta, integrins in vivo" by von Adrian et al. in *Proc. Natl. Acad. Sci. USA* (1991) 88:7538–7542.
"Differential expression of homing-associated adhesion molecules by T cell subsets in man" by Picker et al. in *J. Immunol.* (1990) 145:3247–3255.
F. W. Luscinskas et al, FASEB J5(6), A1602, 1991.
M. Berg et al, *Blood*, 76, 2381–2388, 1990.

*Primary Examiner*—David Saunders
*Attorney, Agent, or Firm*—Bertram I. Rowland

[57] ABSTRACT

Methods and compositions are provided for determining neutrophil activation in a mammalian host by detecting the presence of shed LECAM-1 in the blood. By employing a monoclonal antibody which binds to a common epitope of lymphocyte and neutrophil LECAM-1 and a monoclonal antibody which binds to a sialylated Lewis X epitope which distinguishes between neutrophil and lymphocyte LECAM-1, the level of neutrophil activation can be determined. Various immunoassay protocols may be employed which detect the binding of the two antibodies to a common antigen.

9 Claims, No Drawings

NEUTROPHIL LECAM-1 AS INDICATOR OF NEUTROPHIL ACTIVATION

TECHNICAL FIELD

The field of this invention is detection of neutrophil activation.

BACKGROUND

Blood cells are the primary guardians against diseased states, both as a result of pathogens and cellular aberration. Cells of both the lymphoid and myeloid lineages are involved with the monitoring of the health of the host. Because of the diversity of situations involved with protecting the host, a variety of mechanisms have evolved. While some of the mechanisms are selective, other mechanisms are non-selective in their mode of attack. Thus, not only can the disease associated component be attacked, but also native tissue. Particularly, neutrophils employ a variety of mechanisms for cytotoxicity which are non-selective. In many situations, it would be of interest to know whether neutrophils have become activated to determine whether the body is responding to a particular event, either constructively or destructively.

RELEVANT LITERATURE

LECAM-1 participates in PMN-EC (polymorphonuclear neutrophil—endothelial cell) recognition adhesion. Lewisohn et al., J. Immunol. 138:4313–4321; Jutia et al., (1989) J. Immunol. 143:3318–3324; Hollman et al., (1991) Biochem. Biophys. Res. Comm. 174:236–243; Smith et al., (1991) J. Clin. Invest. 87:609–618. LECAM-1 appears to be involved in an early adhesive event between PMN's and ECs. Atherton and Born, (1972) J. Physiol. 222:447–474. LECAM-1 specific Mabs reproducibly inhibit PMN binding to ELAM-1 transfected L-cells. Kishimoto et al., (1991) Blood, in press. LECAM-1+ lymphocytes bind at best poorly to ELAM-1. Picker et al., (1991) Nature 349:788–799.

SUMMARY OF THE INVENTION

Activated neutrophils are detected by diagnosing for the presence of neutrophil LECAM-1 by using dual monoclonal antibodies, which provide for separation of LECAM-1 and detection of an epitope specific for neutrophil LECAM-1. The detection of shed neutrophil LECAM-1 in blood can be related to neutrophil activation. The knowledge of neutrophil activation may be related to various therapies.

DESCRIPTION OF THE SPECIFIC EMBODIMENTS

Methods and compositions are provided for the determination of the presence of activated neutrophils. The existence or absence of activated neutrophils is related to the presence of soluble neutrophil LECAM-1 in blood. This is determined by providing for the binding of dual monoclonal antibodies, one for an epitope of LECAM-1 common to lymphocytes and neutrophils, and the other for an epitope specific for neutrophil LECAM-1. By detecting the dual binding to a single analyte molecule, one can determine the level of neutrophil LECAM-1 in blood and relate this to the level of neutrophil activation in the host. Particularly, the neutrophil LECAM-1 epitope will be a saccharide epitope associated with sLe$^x$ in sialylated Lewis X antigen.

A blood sample may be taken and be used directly, filtered to remove red blood cells, or subjected to other treatments to provide for serum or plasma or remove any interfering components. The sample may then be used for the assay.

In many instances, the sample will be subject to dilution with an assay medium, buffered at a pH in the range of about 5.5–9, more usually 6.5–8, preferably at about 7–7.5. Various buffers may be used, such as Tris, phosphate, Mops, Hepes, carbonate, etc. Usually, the dilution will vary from about 1–100:1. The sample volume may range from about 0.5–100 μl. The assay medium will generally be from about 10–500 μl.

A large number of assays using a variety of techniques are available for detecting specific epitopes. The assays may be homogeneous or heterogeneous. Labels for detection may include enzymes, fluorophores, luminescers, colored particles, or any other label which would allow for detection of its presence, either visually or by instrumentation.

Conveniently, a sandwich assay may be employed where one may use the combination of antibodies, one as a capture antibody and the other as the labeled antibody. Thus, anti-LECAM-1 may be bound to a surface, while anti-neutrophil LECAM-1 may be dispersed in solution or vice-versa. The dispersed antibody may be labeled or unlabeled, where a second binding member specific for the dispersed antibody and conjugated to a detectable label may be employed.

The dispersed antibody may be modified by a molecule such as biotin to allow for labeled strept/avidin or other ligand which may bind to a receptor, e.g., hapten-antibody, ligand-naturally occurring receptor, etc. Alternatively, one may employ a protein, such as S. aureus protein A, which binds to specific Fc isotypes, where the protein A would be labeled. By using this form of indirect labelling, a much higher level of label may be obtained per binding event.

The bound antibody may be bound to any convenient surface, which may include container walls, e.g. microtiter plate wells, tubes, etc., particles, such as latex particles, magnetic particles, etc., capillary tubes, plates, or the like. The literature is extensive concerning the ways in which antibodies may be bound to a surface. Numerous surfaces are available commercially which are activated or activatable for binding to proteins. Surfaces having carboxylic acids present on the surface may be activated with carbodiimide, carbonyl diimidazole, alcohols or phenols capable of forming esters for reaction in water, e.g. dinitrophenol, pentachlorophenol, N-hydroxy succinimide, etc. Cyanogen bromide may be used to activate surfaces having hydroxylic groups. Mercaptans can be used for reacting with activated olefins or with other mercaptans to form disulfides. The particular manner of binding the antibody to the surface is not critical to this invention. Usually, the surface will be washed with protein which is innocuous for the purposes of the assay and/or a reagent which will react with any unreacted activated groups to prevent non-specific reaction, as well as non-specific binding.

The dispersed antibody may or may not be labeled, where the label may be capable of providing a signal or capable of binding to another compound which provides for the detection of the detectable signal. Thus, unmodified or modified antibody ("antibody conjugate") may be employed for the assay. Where indirect labeling is employed, the indirect label may be combined with the dispersed antibody in a single container, or preferably, may be added subsequently, after the dispersed antibody has been combined with the sample.

Other techniques may be employed, such as channeling, or quenching: in channeling, a homogeneous assay will be involved. Thus, by having the anti-LECAM-1 antibody and the anti-neutrophil-LECAM-1 antibody labeled with enzymes, where the enzyme product of one is the substrate of the other, one can detect the presence of the two enzymes in proximity by the rate of production of the final product For quenching, one antibody has a fluorescer and the other a quencher. See, for example, U.S. Pat. Nos. 4,174,384 and 4,233,402. Numerous other techniques have been described in the literature, which allow for detection of the presence or proximity of two labels as the result of two antibodies binding to a single molecule or aggregation. Any of these techniques may be used with advantage for the subject assay.

The particular order of addition of the various components of the assay medium will depend upon the nature of the assay. In the sandwich assay, one may combine the sample with the bound dispersed antibody sequentially in the assay medium. Using the bound antibody first will limit the proteins which are available for binding to the dispersed antibody. Using the dispersed antibody first will allow for relatively rapid reaction. The bound antibody will usually be in substantial excess to the anticipated maximum amount of antigen. Normally, the amount of dispersed antibody will be at least equal to the anticipated level of the target antigen, more usually in substantial excess, usually at least two-fold excess, and maybe in five-fold excess or more. However, where one is not concerned with a quantitative determination of the amount of neutrophil LECAM-1 in the sample, in some instances, one may have less than stoichimetric based on anticipated levels. Usually, there will be an incubation time of sample and antibody of at least about 0.5 min., more usually at least about 15 min., conveniently at ambient conditions. After the incubation, the sample may then be added to the other antibody and a second incubation carried out. The incubation times for reaction occurring at the surface may be the same or somewhat longer, usually not more than about 1 h, than the incubation time for reaction occurring in solution. After sufficient time for reaction to have occurred between any of the target antigen and the bound antibody, depending on whether addition is simultaneous or sequential, the supernatant may be discarded and the surface washed free of non-specifically bound dispersed antibody.

Where indirect labeling is employed, one will then add the indirect label, provide for an additional incubation, usually not exceeding the previous incubation in time, frequently being less, where the amount of indirect label added may be in substantial excess of the amount required, usually in at least about two-fold excess, to greatly enhance the rate at which binding occurs. After sufficient time for binding of the indirect label, the surface will be washed again to remove any non-specifically bound label and the amount of label on the surface determined.

For an enzyme label, one would normally add the appropriate substrate, particularly a chromogenic or fluorogenic substrate, where the product of the enzymatic reaction produces a detectable product. Where the label is a fluorescent molecule, the fluorescence of the surface may be readily determined using a fluorimeter. For luminescence, the additional reagents necessary to induce luminescence or radiation will be applied to the surface, and the photons which are emitted are counted.

The determination of the presence or absence of neutrophil activation may be related to a variety of situations. In those situations where a patient is exposed to pathogens, it may be of interest to determine whether there has been a neutrophil response. In the case of autoimmune diseases, the chronic nature of the autoimmune disease may be followed by the presence of activiated neutrophils. The presence of activated neutrophils in case of reperfusion can also be of interest in the manner of treatment and outcome of surgery. Thus, there are a number of clinical settings in which there is an interest in being able to determine neutrophil activation.

EXPERIMENTAL

Cells: polymorphonuclear leukocytes (PMN) were isolated from venous blood of healthy adults by centrifugation of diluted blood (1:4 in Hanks Balanced Salt Solution, HBSS) over ficoll-hypaque (Histopaque 1077; Sigma Chemical Co., St. Louis, Mo.) followed by dextran sedimentation of the high density pellet. PMN were washed twice in HBSS and were either used immediately or held at 0°-4° C. in HBSS with 12 mM Hepes (pH 7.2). For some experiments, PMN were fixed with 0.9% paraformaldehyde ($10^6$ cells/ml, 30 mins. at 0° C.), followed by washing with 20% Newborn Calf Serum (NCS) in Dulbecco's Modified Eagles medium (DMEM) prior to use. For other experiments, the isolated PMN were treated with low dose chymotrypsin [type IV (Sigma C-4159) 0.03–0.06 units/$10^6$ PMN] for 5 min. at 37° C. The reaction was stopped with 20% NCS in DMEM (at 0°-4° C.), and the cells were washed ×3 at 4° prior to use. PMN treated identically, but without the chymotrypsin, were used as controls.

Tonsil lymphocytes were prepared by gentle mincing of fresh pediatric tonsil specimens over a type 304 steel screen (Tylinter, Mentor, OH), followed by ficoll-hypaque density centrifugation. Preparations obtained in this manner generally contained about 60–70% B-cells and 30–40% T-cells without detectable PMN (as analyzed by flow cytometry).

ELAM-1 and GMP-140 transfected COS cells were obtained using the DEAE-Dextran transfection method, as previously described (Picker et al, (1991) Nature 349:796–799). GMP-140 cDNA was derived by polymerase chain reaction (PCR) amplification from a phorbol ester-treated human erythroleukemia cell line (HEL 92.1.7) CDNA library using oligonucleotides corresponding to the published 5' and 3' coding sequences of this molecule (Johnston et al., (1989) Cell 56:1033–1044). The specificity of the GMP-140 cDNAs was confirmed by restriction analysis and partial nucleotide sequencing. Furthermore, COS cells transfected with the GMP-140 clone stained specifically with a panel of GMP-140 specific antibodies. ELAM-1 cDNA in the cDM8 expression vector was obtained from Dr. B. Seed (Harvard University), and was also obtained by PCR amplification, as previously described (Picker et al., (1991) Nature 349:796–799). Both ELAM-1 cDNAs gave identical results in adhesion assays. COS cells that were 'mock'-transfected under the same conditions as above, except no DNA was added, were used as a control. Typically, 20–40% of the COS cell population expressed the appropriate adhesion molecule after transfection with either the ELAM-1 or GMP-140 cDNAs, as judged by immunofluorescence with the appropriate mAb.

The production of stable ELAM-1 transfectants using the mouse pre-B cell line L1-2 was performed as follows. Briefly, the ELAM-1 gene was inserted downstream of the hCMV promoter in the pMRB101 vector (a derivative of EE6 which contains the *E. coli* gpt gene; Mulligan and Berg, (1980) Mol. Cell. Biol. 1:449–459); Stephens and Cockett, (1989) Nucleic Acids Res. 17:7110). L1-2 cells were transfected by electroporation, and expressing cells were selected for resistance to mycophenolic acid. ELAM$^{bright}$ cells were selected by cell sorting and cloned by limiting dilution (L1-2$^{ELAM-1}$). For a control, L1-2 cells were transfected with the vector alone (L1-2$^{vector}$). In terms of a variety of cell surface molecules, these cells appear to differ from L1-2$^{ELAM-1}$ only in their expression of ELAM-1.

MAbs: The production and characterization of the Dreg-56 and Dreg-200 mAbs against human LECAM-1 has been described previously (Kishimoto et al., (1990) PNAS USA 87:2244–2248). The CL2 and CL3 mAbs against ELAM-1 (Kishimoto et al., (1991) Blood, in press; Picker et al., (1991) Nature 349:796–799) were a generous gift of Dr. C. W. Smith. The phycoerythrin (PE)-conjugated anti-LECAM-1 mAb Leu 8 and PE-conjugated mouse IgG control, used in the immunofluorescence analysis, was obtained from Becton Dickinson Immunocytometry Systems (San Jose, Calif.). MAb 60.3 (against CD18; Dobrina et al., (1989) Immunol. 67:502–508) was kindly provided by Dr. J. Harlan (U. of Washington, Seattle). MAb BB7.5, against MHC class I, was produced from the American Type Culture Collection (ATCC) HB120 hybridoma. A variety of mouse IgG mAbs were used as controls for the mouse IgG experimental mAbs. PJ-2 and PJ-18 (against irrelevant human EC antigens) were used as controls for the western blot analysis. For functional studies (where PMN binding controls were desirable), either L3B12 (anti-CD45; Wood, et al., (1984) Am. J. Clin. Pathol. 81:176–183) or PJ-32 were used. PJ-32 recognizes a high-density PMN surface antigen (Hallman et al., (1991) Biochem. Biophys. Res. Commun. 174;236–243) that lacks modification with sLeX. MAb CSLEX-1 (mouse IgM), against sLeX (Fukushima et al., (1984) Cancer Res. 44:5279–5285), was produced from the CSLEX-1 hybridoma obtained from the ATCC (HB-8580). The murine IgM myeloma protein TEPC-183 (Sigma) was used as a class matched control for CSLEX-1.

MAb HECA-452 (a rat IgM) was developed and characterized in our own laboratory (Duijvestijn et al., (1988) Am. J. Patnol. 130:147–155); Picker et al., 1990 and 1991, supra). This mAB recognizes sLeX and related carbohydrate ligands for ELAM-1 including the T-cell ELAM-1 ligand, CLA. Briefly, HECA-452 binds a periodate- and neuraminidase-sensitive epitope expressed on PMN, monocytes, and a subset of memory T-cells (the CLA+ skin-associated T-cell subset), all subsets that bind ELAM-1. It also recognizes HEV, the significance of which is not known. Affinity-isolated HECA-452 Ag from a variety of cell types supports the specific binding of ELAM-1 transfected L1-2 cells, an interaction that is also blocked by this monoclonal antibody. HECA-452 and CSLEX-1 show similar patterns of staining on western blot analysis of PMN glycoproteins, and HECA-452 specifically immunoprecipitates CSLEX-1-reactive glycoproteins. HECA-452 has also been shown to directly recognize sLeX glycoconjugates by ELISA. HECA-452 reactivity appears to parallel ELAM-1 binding more closely than CSLEX-1, in that HECA-452 recognizes the T-cell ELAM-1 ligand CLA, whereas CSLEX-1 stains only a minor subset of CLA+ T-cells. For immunofluorescence studies, FITC-conjugated HECA-452 was used as previously described (Picker et al., 1990 and 1991, supra). MAbs OZ-42, AT83A, and MECA-79 (all rat IgMs direct against irrelevant epitopes) were used as class-matched negative controls for this mAb.

Flow Cytometry: Cell populations (0.5–1×10$^6$ cells/test) were incubated with appropriately titered PE-conjugated and/or FITC-conjugated mAbs for 30 minutes at 0°–4° C., washed with Dulbecco's phosphate buffered saline (PBS) containing 0.1% bovine serum albumin, and either analyzed immediately, or fixed in PBS containing 1% paraformaldehyde and saved at 4° C. for later analysis. Samples were examined on a FAC-Scan flow cytometer (Becton Dickinson Immunocytometry Systems, Mountain View, Calif.), and data were analyzed using Consort 30 and LYSYS software (BDIS), as previously described (Picker et al., 1990, supra).

Lysate Preparation/Immunoprecipitation: Lysates were prepared by incubating cells (PMN or tonsil lymphocytes at 5×10$^7$ /ml) in lysis buffer [2% Nonidet P-40, 150 mM NaCl, 1 mM MgCl$_2$, 10 μg/ml each of pepstatin, leupeptin, chymostatin, antipain, benzamidine hydrochloride, 1,10-phenanthroline, and 1 mM phenylmethylsulphonyl fluoride (PMSF) in 20 mM Tris-HCl, pH 7.5] for 30 minutes at 4° C., followed by centrifugation (48,000×g for 30 minutes at 4° C.), and passage through 0.2 μm filters (Nalge, Rochester, N.Y.). All mAbs were coupled to CNBr-activated Sepharose 4B (Pharmacia, Uppsala, Sweden; 2 mg Ig per ml Sepharose) per the manufacturers instructions. For immunoprecipitations, lysates were incubated with 25 μl of MAb-conjugated Sepharose/ml lysate, rotating, at 4° C. for 4 hrs. to overnight. Typically, 10 ml of a given lysate was precleared 1–3× with Sepharose conjugated to appropriate control mAbs, followed by immunoprecipitation with the mAb of interest. Pellets were washed 3–4× with NP-40 wash buffer (20 mM Tris-HCl, pH 7.5 containing 500 mM NaCl, 1 mM MgCl$_2$, 1 mM PMSF, 0.02% NaN$_3$, and 0.1% NP-40), and then solubilized directly in Laemmli's buffer prior to SDS-PAGE electrophoresis (see below). For preclearing experiments, lysates were exposed to 3–4 cycles of incubation with 50 μl of mAb-conjugated Sepharose/ml of lysate per cycle (each cycle 8–12 hours, rotating at 4° C.).

Antigen Preparation/Quantitation: LECAM-1 antigen was isolated by passage of the crude PMN or tonsil lymphocyte lysates (120–150 ml of lysate for each; prepared as described above) over a precolumn of a control mAb (see below) coupled to Sepharose 4B (prepared as described above), followed by a Dreg-56 Sepharose column (1.0 ml columns). After passage through the Dreg-56 column, tonsil lymphocyte lysates were passed over a HECA-452 column to obtain positive control Ag preparations for ELAM-1 binding. MAb PJ-32 was used in precolumns exposed to PMN lysates as a source of control Ag (PJ-32 reacts with a high density PMN Ag that lacks modification with CSLEX-1 or HECA-452 reactive determinants). Columns were extensively washed with β-octylglucoside wash buffer (same as the NP-40 wash buffer described above except that the NP-40 detergent is replaced with 50 mM β-octylglucoside), and were eluted with 500 mM NaCl, 0.02% NaN$_3$, 1 mM PMSF and 50 mM β-octylglucoside in 200 mM acetic acid. The eluted fractions (0.8 ml) were neutralized with 0.25 ml of 1 M Tris-HCl, pH 8.2, and were then assayed for LECAM-1 and other Ags by dot-blot analysis (Picker et al., (1989), supra) using the relevant detection mAbs.

The initial quantitation of LECAM-1 and sLeX immunoreactivity in peak fractions was performed with dot blot analysis of serial dilutions using the Dreg-56 and HECA-452 mAbs vs. isotype-matched controls (1 μl aliquots of serial dilutions of antigen preparations blotted on nitrocellulose and compared for maximum dilution giving detectable reactivity). After initial concentration adjustment, all preparations were re-analyzed by a precise ELISA using Dreg-200, HECA-452, CSLEX-1, and isotype-matched controls-as primary detection mAbs. ELISAs were performed on serial dilutions of the Ag (in triplicate) directly adsorbed to the 96 well plates (5λ of the diluted Ag prep. added to 45λ dH$_2$0, incubated overnight at 4° C.). After Ag binding, the plates were blocked with 1% BSA in dPBS [1 hr.; at room temperature (RT)] and then incubated sequentially (1-2 hrs; RT) with appropriately titered 1° mAbs, biotinylated 2° Abs [goat anti-mouse Ig (Zymed Labs, San Francisco, Calif.) and anti-rat IgM (KPL Labs, Gaithersburg, Md.)], and horseradish peroxidase-conjugated Streptavidin (Zymed), followed by development of the peroxidase reaction and determination of the OD at 490 nm (procedure adapted from Staehelin et al., (1981) Methods Enzymol. 79:589–594). PMN and tonsil lymphocyte LECAM-1 preparations were normalized such that equivalent dilutions gave a ½ maximal response in OD at 490 nm using the Dreg-200 mAb.

Electrophoretic Procedures/Western Blotting: Aliquots of crude lysates, immunoprecipitates or affinity isolated LECAM-1 antigen preparations were applied to 8% SDS-PAGE gels as previously described (Picker et al., 1989 and 1990, supra). To preserve optimal antigenicity for western blotting, samples were heated to 42° for 20 mins rather than boiling, and gels were run under non-reducing conditions. Western blot analysis was performed using an indirect alkaline phosphatase immunodetection system (Picker et al., 1989 and 1990, supra). For total glycoprotein analysis, purified LECAM-1 preparations were run on 8% SDS-PAGE gels under reducing conditions. After transfer to nitrocellulose, total glycoproteins were visualized using the digoxigenin labeling/anti-digoxigenin immunodetection technique, as described in the Boehringer Mannheim (Indianapolis, Ind.) glycan detection kit.

Adhesion Assays: The ability of isolated glycoproteins to support the binding of L1-2$^{ELAM-1}$ vs. L1-2$^{control}$ was assayed as previously described (Berg et al., (1991) J. Cell. Biol., in press). Briefly, affinity isolated preparations of LECAM-1 or control glycoproteins were absorbed onto the wells of LAB-Tek slides (Nunc., Inc., Naperville, Ill.) by diluting the Ag preparations below the critical micellar concentration of the β-octylglucoside detergent (usually 1:7) with DMEM containing 12 mM Hepes buffer, pH 7.0, and incubating overnight at 4° C. After blocking in DMAM/Hepes with 5% NCS, L1-2$^{ELAM-1}$ or L1-2$^{control}$ cells were applied to each well (2.2×10$^6$ cells in 0.15 ml), and incubated 25 minutes at RT on a rotary shaker (at 60 r.p.m.). The tops of the wells were removed and the slides were washed by immersion in DMEM/Hepes×3, and then fixed in 1.5% glutaraldehyde in DMEM. For mAb inhibition experiments, the L1-2$^{ELAM-1}$ cells or wells (as appropriate) were pre-incubated with mAbs (1-2 μg mAb/10$^6$ cells or 20 μg/well) for 20 minutes (0° C. for cells, RT for wells). MAbs were washed away immediately prior to the adhesion assay. After fixation, the number of cells per unit area were quantitated by light microscopy. Five to ten 1 mm$^2$ fields were counted per well, and all determinations were assessed with triplicate wells.

The assay used to assess PMN binding to ELAM-1 and GMP-140 transfected COS cells has also been previously described (Picker et al., (1991) supra). Briefly, 2×10$^6$ s PMN (fresh, fixed, chymotrypsin vs. control treated, or mAb-treated) in 2 ml of DMEM/Hepes were added to subconfluent cultures of ELAM-1-, GMP-140-, or mock-transfected COS cells in 60 mm culture dishes, and incubated on a rotary shaker (60 r.p.m.) for 25 minutes at RT. After washing ×3 with DMEM/Hepes, adherent cells were fixed with 1.5% glutaraldehyde in DMEM, and quantitated by light microscopy. Both the number of COS cells and PMN bound to COS cells were enumerated per 0.25 mm$^2$ field, counting 15-25 fields per plate (each determination with triplicate plates). The transfected COS cells were combined and replated 24 hrs. prior to the adhesion assays in order to insure an even distribution of the transfectants. PMN binding to plastic or to mock-transfectants was negligible under the conditions of this assay, and identical results were obtained enumerating the binding as PMN/COS cell or PMN/user area. For mAb inhibition studies, PMN were pretreated for 20 mins. with 2 μg mAb/10$^6$ PMN at 0° C.

RESULTS Anti-LECAM-1 MAbs Inhibit PMN Binding to ELAM-1 Transfectants

The participation of LECAM-1 in ELAM-1-mediated PMN adhesion to EC was first suggested by experiments demonstrating that LECAM-1-specific mAbs could inhibit PMN binding to ELAM-1 transfected L-cells by 50-60% (Kishimoto et al., (1991), Blood, in press). We have confirmed this observation in a COS transfection system, showing that the Dreg-56 mAb against LECAM-1 reproducibly inhibits PMN binding to ELAM-1 transfectants by 50±5% (compared to class-matched control mAb; mean ±S.E.; n=5). This inhibition does not appear to be due to a mAb-induced signaling phenomenon resulting in down-regulation of distinct ELAM-1 ligands, since we have found similar inhibition (41±5%; n=3) using paraformaldehyde-fixed PMN in these adhesion assays.

PMN, But Not Lymphocyte, LECAM-1 Is Decorated by Oligosaccharide Ligands for ELAM-1

The direct involvement of anti-LECAM-1 in neutrophil recognition of ELAM-1 could be explained, at least in part, if ELAM-1 bound to carbohydrate ligands on LECAM-1. ELAM-1 has been shown to recognize sialylated, fucosylated lactosamines including sLeX (Lowe et al., (1990) Cell 63:475–484; Phillips et al., (1990) Science 250:1130–1132; Goelz et al., (1990) Cell 63:1349–1356; Walz et al., (1990) Science 250:1132–1135; Brandley et al., (1990) Cell 63:861–863). The cutaneous lymphocyte antigen, CLA, is a skin lymphocyte homing receptor for the vascular lectin ELAM-1. The availability of mAbs specific for these oligosaccharide ELAM-1 ligands—HECA-452 and CSLEX-1 (see Procedures section)—allowed us to investigate immunochemically the possibility that PMN LECAM-1 was "decorated" with these structures. On western blots of whole PMN lysates, mAb HECA-452 recognizes a broad array of bands at $M_r$ ranging from 50-180 kD (Picker et al., (1990) Am. J. Pathol. 136:1053-1068), including a band at about 85-95 kD that co-migrates with PMN LECAM-1. Preclearing PMN lysates with mAb Dreg-56, against LECAM-1, specifically removes this HECA-452-reactive band. Densitometric comparison of HECA-452 reactivity in immunoblots of control and Dreg-56 precleared lysates indicates that 5% or less of HECA-452 reactivity in the 50-200kD $M_r$ range is associated with mAb Dreg-56-defined LECAM-1. Western analyses of LECAM-1 immunoprecipitates revealed that PMN, but not tonsil lymphocyte, LECAM-1 was modified with HECA-452 (and CSLEX-1) reactive determinants. Reciprocally, HECA-452 immunoprecipitates of PMN, but not lymphocyte lysates contained co-precipitated LECAM-1. These findings were confirmed more quantitatively by ELISA analysis of affinity-purified PMN and tonsil lymphocyte LECAM-1. Again, PMN LECAM-1, but not lymphocyte LECAM-1, displayed reactivity with HECA-452 and CSLEX-1 mAbs. Thus, although other glycoprotein species also bear high levels of sLeX, LECAM-1 is one major neutrophil glycoprotein decorated by these carbohydrate ligands. This modification is neutrophil-selective, as lymphocyte LECAM-1 is not detectably recognized by sLeX-reactive mAbs.

Purified PMN, But Not Lymphocyte, LECAM-1 Binds ELAM-1 Transfectants

In order to substantiate the functional significance of the immunochemical demonstration of putative ELAM-1 ligands on LECAM-1, we examined the ability of purified PMN and lymphocyte LECAM-1 to support the binding of ELAM-1 transfected L1-2 cells. PMN LECAM-1 adsorbed to plastic supported the binding of L1-2$^{ELAM-1}$ cells, but not the control L1-2$^{vector}$. In contrast, lymphocyte LECAM-1 preparations, adjusted to identical titers of LECAM-1 immunoreactivity, lacked this ability. PMN LECAM-1 preparations could be diluted 8-10 fold and still show significant ELAM-1 binding over background, indicating that minor differences in LECAM-1 concentration did not account for the inability of lymphocyte LECAM-1 to interact With ELAM-1. PJ-32 Ag, a high density PMN cell surface Ag that lacks CSLEX-1 or HECA-452 immunoreactivity, did not support L1-2$^{ELAM-1}$ binding, whereas, in agreement with previous studies, tonsil lymphocyte HECA-452 Ag isolated from the same lysate as the lymphocyte LECAM-1 preparations did mediate specific L1-2$^{ELAM-1}$ binding. Indeed, when adjusted to equivalent HECA-452 immunoreactivity (measured by ELISA), PMN LECAM-1 and tonsil lymphocyte HECA-452 Ag demonstrated quantitatively similar binding to the ELAM-1 transfectants.

The specificity of the interaction between isolated PMN LECAM-1 and L1-2$^{ELAM-1}$ was confirmed with mAb-inhibition studies. Pretreatment of the L1-2$^{ELAM-1}$ cells with mAbs against ELAM-1 (mAbs CL2 and CL3) completely abrogated the specific interaction between isolated PMN LECAM-1 and the ELAM-1 transfectants. Pretreatment of the adsorbed LECAM-1 with either the HECA-452 or CSLEX-1 mAbs, but not isotype-matched control mAbs, inhibited binding by over 70%. Significantly, pretreatment of the PMN LECAM-1-coated slides with mAbs against LECAM-1 epitopes common to both PMN and lymphocytes (i.e. mAbs not primarily recognizing specific oligosaccharide epitopes; Dreg-56 and Dreg-200) also resulted in nearly 60% inhibition of L1-2$^{ELAM-1}$ binding. These results clearly demonstrate that PMN, but not lymphocyte, LECAM-1 is an ELAM-1 counter-receptor, and that anti-LECAM-1 mAbs, against common LECAM-1 determinants, can interfere with this interaction.

Removal of LECAM-1-Associated sLeX Reduces ELAM-1 Binding by Intact PMN

The ability of LECAM-1-specific mAbs to inhibit 50% or more of the binding between viable PMN and ELAM-1 transfected COS cells—when only a small percentage of potential ELAM-1 ligands is associated with LECAM-1—suggests a unique functional importance for LECAM-1-associated oligosaccharides. In other words, LECAM-1 on intact PMN may be a "preferential presenter" of sLeX determinants to cell-associated ELAM-1; sLeX determinants associated with other structures may be functionally less efficient that LECAM-1-associated sLeX, or perhaps, are relatively inaccessible to cell-associated ELAM-1. To investigate this hypothesis, we made use of the observation that short incubations with very low doses of chymotrypsin selectively cleaves LECAM-1 from the PMN surface. At levels of chymotrypsin that effectively remove surface LECAM-1 from PMN (0.03-0.06 units/$10^6$ cells for 5'), no alterations in PMN viability, morphology, binding to plastic, random migration, and expression of a variety of PMN cell surface molecules (including CD11b, CD16, CD44, CD45RA, SK 105 Ag, and RB6-8C5 Ag) are detectable. While other PMN cell surface molecules may be affected by this treatment, there is no detectable effect on surface expression of immunologically-defined carbohydrate ligands for ELAM-1. In 3 experiments, the mean fluorescent intensity ($\pm$S.E.M.) of PMN stained with FITC-HECA-452 did not detectably change (99$\pm$8% of control values) under conditions which removed over 90% of the cell surface LECAM-1 (mean fluorescent intenity $\pm$S.E.M. for PE-conjugated anti-Leu 8 staining: 7$\pm$3% of control in the same experiments). In addition, chymotrypsin treatment had no discernible effect on HECA-452-reactive PMN glycoproteins in western blot analyses, except for the loss of the HECA-452-reactive band corresponding to LECAM-1. Despite this retention of immunoreactive carbohydrate ELAM-1 ligands, chymotrypsin-treated PMN showed a marked defect in their ability to recognize and bind ELAM-1 transfected COS cells under conditions of shear, similar to the inhibition observed when saturating levels of LECAM-1 specific mAbs are present (68$\pm$1% binding inhibition for chymotrypsin-treated PMN vs. 61$\pm$4% inhibition with the Dreg-56 mAb analyzed in the same experiments; n=3). These data do not exclude the possibility that other (non-LECAM-1) sLeX-bearing cell surface molecules are active in PMN recognition of ELAM-1, but they are supportive of the hypothesis that PMN LECAM-1 plays a major, perhaps predominant, role in presenting sLeX and/or related oligosaccharide determinants to cell-associated ELAM-1 under conditions of shear.

The subject invention allows for the determination of the activation state of neutrophils in a mammalian host, where the activation may be related to the health of the individual or directs a particular mode of treatment. Since neutrophils are associated with the defensive mechanisms associated with disease, the knowledge that neutrophils are not responding to the invasion by a pathogen will direct particular treatments. Similarly, if neutrophils are involved in the pathogenesis of a diseased condition, action can be taken to inhibit neutrophil activation. Thus, knowledge of the state of neutrophils, whether quiescent or activated, can be important in the diagnosis and prognosis of disease and in the choice of treatment.

All publications and patent applications mentioned in this specification are indicative of the level of skill of those skilled in the art to which this invention pertains. All publications and patent applications are herein incorporated by reference to the same extent as if each individual publication or patent application was specifically and individually indicted to be incorporated by reference.

Although the foregoing invention has been described in some detail by way of illustration and example for purposes of clarity of understanding, it will be understood that certain changes and modifications may be practiced within the scope of the appended claims.

What is claimed is:

1. A method of detecting neutrophil activation in a mammalian host, said method comprising:
   combining a blood sample with a first antibody specific for an epitope common to neutrophil and lymphocyte LECAM-1 and a second antibody specific for a sialylated Lewis X epitope on neutrophil LECAM-1 and not lymphocyte LECAM-1; and
   detecting the presence of a complex between an antigen and said first and second antibodies as indicative of neutrophil activation.

2. A method according to claim 1, wherein said blood sample is combined with said first antibody before being combined with said second antibody.

3. A method of detecting neutrophil activation in a mammalian host, said method comprising:
   combining a blood sample with a first antibody specific for an epitope common to neutrophil and lymphocyte LECAM-1 and bound to a surface and a second antibody specific for a sialylated Lewis X epitope on neutrophil LECAM-1 and not lymphocyte LECAM-1 dispersed in solution; and
   detecting the presence of a complex between an antigen and said first and second antibodies as indicative of neutrophil activation by means of a label bound directly or indirectly to said second antibody.

4. A method according to claim 3, wherein said blood sample is combined with said first antibody in a first step; and including the additional step of washing said surface free of non-specifically bound components of said sample prior to addition of said second antibody.

5. A method according to claim 4, including the additional step of adding said second antibody after said washing, followed by washing said surface free of non-specifically bound second antibody.

6. A method according to claim 3, wherein said detecting is by means of an enzyme label.

7. A kit comprising a first monoclonal antibody binding to LECAM-1 from neutrophils and lymphocytes, a second monoclonal antibody binding to a sialylated Lewis X epitope of LECAM-1 from neutrophils and not from lymphocytes, wherein one of said antibodies is bound to a surface.

8. A kit according to claim 7, wherein said first antibody is bound to said surface and said second antibody is conjugated to a detectable label or said kit further includes a labeled conjugate capable of binding to said second antibody and not said first antibody.

9. A kit according to claim 8, wherein said label is an enzyme.

* * * * *

UNITED STATES PATENT AND TRADEMARK OFFICE
CERTIFICATE OF CORRECTION

PATENT NO. : 5,316,913

DATED : September 6, 1991

INVENTOR(S) : EUGENE C. BUTCHER; LOUIS J. PICKER

It is certified that error appears in the above-identified patent and that said Letters Patent is hereby corrected as shown below:

Column 1, line 5

--This invention was made with Government support under NIH Grant No. AI9957. The Government has certain rights in this inmention.--

Signed and Sealed this

Twenty-ninth Day of November, 1994

Attest:

BRUCE LEHMAN

Attesting Officer

Commissioner of Patents and Trademarks